(12) United States Patent
Bi et al.

(10) Patent No.: US 11,203,563 B2
(45) Date of Patent: Dec. 21, 2021

(54) PREPARATION OF ZINC LINOLENATE, AND APPLICATION OF ZINC LINOLENATE IN PREPARING ANTI-HELICOBACTER PYLORI DRUG

(71) Applicant: NANJING MEDICAL UNIVERSITY, Jiangsu (CN)

(72) Inventors: Hongkai Bi, Jiangsu (CN); Yanqiang Huang, Jiangsu (CN); Xudong Hang, Jiangsu (CN); Liping Zeng, Jiangsu (CN); Jia Jia, Jiangsu (CN)

(73) Assignee: NANJING MEDICAL UNIVERSITY, Jiangsu (CN)

( * ) Notice: Subject to any disclaimer, the term of this patent is extended or adjusted under 35 U.S.C. 154(b) by 0 days.

(21) Appl. No.: 17/055,129

(22) PCT Filed: Jul. 4, 2019

(86) PCT No.: PCT/CN2019/094664
§ 371 (c)(1),
(2) Date: Nov. 13, 2020

(87) PCT Pub. No.: WO2019/219093
PCT Pub. Date: Nov. 21, 2019

(65) Prior Publication Data
US 2021/0107854 A1   Apr. 15, 2021

(30) Foreign Application Priority Data
May 15, 2018 (CN) .......................... 201810462768.9

(51) Int. Cl.
  *C07C 51/41*   (2006.01)
  *A61K 33/30*   (2006.01)
  *C07C 57/12*   (2006.01)

(52) U.S. Cl.
  CPC ............ *C07C 51/412* (2013.01); *A61K 33/30* (2013.01); *C07C 57/12* (2013.01)

(58) Field of Classification Search
  CPC ........ A61K 33/30; C07C 57/12; C07C 51/412
  See application file for complete search history.

(56) References Cited

FOREIGN PATENT DOCUMENTS

| CN | 1837177 | 9/2006 |
|---|---|---|
| CN | 108623448 | 10/2018 |
| GB | 2217602 | 11/1989 |

OTHER PUBLICATIONS

"International Search Report (Form PCT/ISA/210) of PCT/CN2019/094664", dated Oct. 9, 2019, with English translation thereof, pp. 1-6.

Yanqiang Huang, et al., "In Vitro and In Vivo Activities of Zinc Linolenate, a Selective Antibacterial Agent against Helicobacter pylori," Antimicrobial Agents and Chemotherapy, vol. 63, Apr. 2019, pp. 1-18.

Yanqiang Huang, et al., "The antibacterial activity of zinc linolenic acid small molecular compounds to Helicobacter pylori." The 13th China Antibiotics Conference, vol. 68, Nov. 2017, pp. 264-265.

*Primary Examiner* — Ana Z Muresan
(74) *Attorney, Agent, or Firm* — JCIP Global Inc.

(57) ABSTRACT

Disclosed are preparation of zinc linolenate, and application thereof in preparing an anti-*Helicobacter pylori* drug. Zinc chloride is dissolved in sterile water, and the zinc chloride solution is heated and activated in a reactor kettle, and then naturally cooled to room temperature; 1-ethyl-3-(3-dimethylaminopropyl)carbodiimide hydrochloride, N-hydroxysulfosuccinimide sodium salt and linolenic acid are dissolved in an EMS solvent and activated in nitrogen gas; the activated zinc chloride and the activated linolenic acid are heated and reacted, then left for standing after the reaction is finished; a dialysis bag is used to perform dialysis in pure water until the pure water is clear and transparent; and a vacuum freeze dryer is used to perform drying, and zinc linolenate is obtained. The present invention successfully prepares zinc linolenate, with high yield, and the zinc linolenate has a good *Helicobacter pylori* inhibiting effect.

4 Claims, 5 Drawing Sheets

PREPARATION OF ZINC LINOLENATE, AND APPLICATION OF ZINC LINOLENATE IN PREPARING ANTI-HELICOBACTER PYLORI DRUG

CROSS-REFERENCE TO RELATED APPLICATION

This application is a 371 of international application of PCT application serial no. PCT/CN2019/094664, filed on Jul. 4, 2019, which claims the priority benefit of China application no. 201810462768.9, filed on May 15, 2018. The entirety of each of the above-mentioned patent applications is hereby incorporated by reference herein and made a part of this specification.

BACKGROUND

Technical Field

The present invention belongs to the field of medicine, and specifically relates to preparation of zinc linolenate, and application of zinc linolenate in preparing an anti-*Helicobacter pylori* drug.

Description of Related Art

*Helicobacter pylori* (Hp) is a gram-negative bacterium with a spiral shape, is microaerobic, and is demanding for growth conditions. Studies have shown that Hp infection can cause acute and chronic gastritis, gastric and duodenal ulcer, lymphoproliferative gastric lymphoma, and other diseases, and are related to gastric cancer, extra-intestinal liver cancer, diabetes, and other diseases. In 1994, the World Health Organization classified Hp as a type I carcinogen, and Hp plays a leading role in the occurrence and development of gastric cancer. At present, the therapeutic regimen for eradication of *H. pylori* is triple or quadruple therapy, i.e. taking a proton pump inhibitor (omeprazole, etc.) plus two antibiotics (two of clarithromycin, amoxicillin, tetracycline, metronidazole, etc.), or bismuth (bismuth potassium citrate, etc.) plus a proton pump inhibitor (omeprazole, etc.) plus two antibiotics (two of clarithromycin, amoxicillin, tetracycline, metronidazole, etc.). However, with the long-term use of antibiotics, Hp has developed different degrees of resistance to antibiotics, leading to failure of the triple or quadruple therapy. In 2017, WHO released 12 key pathogens in urgent need of new antibiotics for treatment, one of which is clarithromycin-resistant *Helicobacter pylori*. Therefore, it has become a very important and urgent task to find new anti-Hp drugs with high efficiency and safety.

SUMMARY

Technical Problem

The present invention provides preparation of zinc linolenate, and application of zinc linolenate in preparing an anti-*Helicobacter pylori* drug. The prepared zinc linolenate has a good inhibiting effect on drug-resistant and sensitive *Helicobacter pylori*.

Technical Solution

A preparation method of zinc linolenate, includes the following steps: step one, activation of zinc chloride:dissolving zinc chloride in sterile water, and reacting the zinc chloride solution in a reactor kettle at 150-170° C. for 30-60 min, and then naturally cooling the zinc chloride solution to room temperature; step two, activation of linolenic acid: dissolving 1-ethyl-3-(3-dimethylaminopropyl)carbodiimide hydrochloride (EDC), N-hydroxysulfosuccinimide sodium salt (NHS) and linolenic acid in a molar ratio of (2-4):(2-4):1 in an EMS solvent and performing activation in nitrogen gas for 30 min; step three, complex reaction: reacting the activated zinc chloride in the step one and the activated linolenic acid in the step two in a molar ratio of 1:(1.8-2) at 70-80° C. for 2-3 h, then leaving the reaction solution for standing for 6-12 h after the reaction is finished; step four, dialysis filtration: performing dialysis using a dialysis bag in pure water for 12-14 h until the pure water is clear and transparent; and step five, freeze drying: performing drying using a vacuum freeze dryer for 48-72 h to obtain zinc linolenate.

Preferably, the concentration of the aqueous solution of zinc chloride is 1 mol/L.

Preferably, the molar ratio of the 1-ethyl-3-(3-dimethylaminopropyl)carbodiimide hydrochloride (EDC) to the N-hydroxysulfosuccinimide sodium salt (NHS) to the linolenic acid is 4:4:1.

Preferably, the molar ratio of the activated zinc chloride to the activated linolenic acid is 1:1.8.

Application of zinc linolenate in preparation of drugs for inhibiting the growth of *Helicobacter pylori*.

Application of zinc linolenate in preparation of drugs for treating acute and chronic gastritis, and gastric and duodenal ulcers caused by drug-resistant or sensitive *Helicobacter pylori* infection.

Advantageous Effects

Firstly, the present invention successfully prepares zinc linolenate with high yield; secondly, the present invention increases new use of the zinc linolenate, i.e., zinc linolenate can be used to inhibit the growth of *Helicobacter pylori*; and thirdly, the zinc linolenate prepared by the present invention can be used to treat acute and chronic gastritis, gastric and duodenal ulcers and other diseases caused by drug-resistant or sensitive *Helicobacter pylori* infection, has high action specificity and small toxic and side effects, is not liable to develop drug resistance, and effectively alleviates drug resistance of *Helicobacter pylori*.

BRIEF DESCRIPTION OF THE DRAWINGS

FIG. 3 shows the repairing effect of zinc linolenate on gastric mucosal inflammation in mice, wherein A is the HE staining image of the gastric mucosa of normal mice, ×100; F is the TUNEL staining image of the gastric mucosa of normal mice, ×100; B is the HE staining image of the gastric mucosa of mice infected with the BHK159 strain and treated with PBS, ×100; G is the TUNEL staining image of the gastric mucosa of mice infected with the BHK159 strain and treated with PBS, ×100; C is the HE staining image of the gastric mucosa of mice infected with the BHK159 strain and treated by omeprazole and zinc linolenate combined therapy, ×100; H is the TUNEL staining image of the gastric mucosa of mice infected with the BHK159 strain and treated by omeprazole and zinc linolenate combined therapy, ×100; D is the HE staining image of the gastric mucosa of mice infected with the BHK159 strain and treated by omeprazole, amoxicillin and clarithromycin triple therapy, ×100; I is the TUNEL staining image of the gastric mucosa of mice infected with the BHK159 strain and treated by omeprazole, amoxicillin and clarithromycin triple therapy, ×100; E is the HE staining image of the gastric mucosa of mice infected with the BHK159 strain and treated by zinc linolenate alone, ×100; and J is the TUNEL staining image of the gastric mucosa of mice infected with the BHK159 strain and treated by zinc linolenate alone, ×100.

DESCRIPTION OF THE EMBODIMENTS

Embodiment 1

Step one, zinc chloride is activated: 1.36 g of zinc chloride is dissolved in 10 mL of sterile water (1 mol/L) in a reactor kettle, and the reactor kettle is placed in a drying box, heated to 160° C., reacted for 30 min, and naturally cooled to room temperature.

Step two, linolenic acid is activated: 766 mg of 1-ethyl-3-(3-dimethylaminopropyl)carbodiimide hydrochloride (EDC), 460 mg of N-hydroxysulfosuccinimide sodium salt (NHS) and 560 mg of α-linolenic acid (α-LLA) are dissolved in 5 mL of EMS solvent and stirred uniformly in nitrogen gas and activated for 30 min.

Step three, a complex reaction is performed: 1 mL (136 mg or 1 mM) of the activated zinc chloride and 5 mL (560 mg or 2 mM) of linolenic acid are added to the reactor kettle, and 4 mL of sterile water is added, 10 mL of liquid in total. The liquid is uniformly mixed on a heated magnetic stirrer. The temperature is controlled at 60° C., and the reaction is performed for 3 h. The reaction solution is left for standing to cool overnight after the reaction is finished.

Step four, dialysis washing is performed: the complex reaction solution is charged into a dialysis bag (RC membrane, 1 KD, 38 mm), and dialyzed with 1 L of deionized water for 12 h. The deionized water is changed 4 times during dialysis, and unbound zinc ions and other impurities are dialyzed and filtered until the deionized water is clear and transparent.

Step five, freeze drying is performed: the dialyzed reaction solution is charged into a glass screw-top sample, and dried with a vacuum freeze dryer at −45° C. and 0.02 mBar for 72 h, and the zinc linolenate is obtained with a yield of 77.2%.

Embodiment 2

Step one, zinc chloride is activated: 1.36 g of zinc chloride is dissolved in 10 mL of sterile water (1 mol/L) in a reactor kettle, and the reactor kettle is placed in a drying box, heated to 165° C., reacted for 30 min, and naturally cooled.

Step two, linolenic acid is activated: 766 mg of 1-ethyl-3-(3-dimethylaminopropyl)carbodiimide hydrochloride (EDC), 460 mg of N-hydroxysulfosuccinimide sodium salt (NHS) and 560 mg of α-linolenic acid (α-LLA) are dissolved in 5 mL of EMS solvent and stirred uniformly in nitrogen gas and activated for 30 min.

Step three, a complex reaction is performed: 1 mL (136 mg or 1 mM) of the activated zinc chloride and 4.5 mL (504 mg or 1.8 mM) of linolenic acid are added to the reactor kettle, and 4.5 mL of sterile water is added, 10 mL of liquid in total. The liquid is uniformly mixed on a heated magnetic stirrer. The temperature is controlled at 70° C., and the reaction is performed for 3 h. The reaction solution is left for standing to cool overnight after the reaction is finished.

Step four, dialysis washing is performed: the complex reaction solution is charged into a dialysis bag (RC membrane, 1 KD, 38 mm), and dialyzed with 1 L of deionized water for 12 h. The deionized water is changed 4 times during dialysis, and unbound zinc ions and other impurities are dialyzed and filtered until the deionized water is clear and transparent.

Step five, freeze drying is performed: the dialyzed reaction solution is charged into a glass screw-top sample bottle, and dried with a vacuum freeze dryer at −45° C. and 0.02 mBar for 72 h, and the zinc linolenate is obtained with a yield of 79.4%.

Embodiment 3

Step one, zinc chloride is activated: 1.36 g of zinc chloride is dissolved in 10 mL of sterile water (1 mol/L) in a reactor kettle, and the reactor kettle is placed in a drying box, heated to 170° C., reacted for 30 min, and naturally cooled.

Step two, linolenic acid is activated: 766 mg of 1-ethyl-3-(3-dimethylaminopropyl)carbodiimide hydrochloride (EDC), 460 mg of N-hydroxysulfosuccinimide sodium salt (NHS) and 560 mg of α-linolenic acid (α-LLA) are dissolved in 5 mL of EMS solvent and stirred uniformly in nitrogen gas and activated for 30 min.

Step three, a complex reaction is performed: 1 mL (136 mg or 1 mM) of the activated zinc chloride and 5 mL (504 mg or 1.8 mM) of linolenic acid are added to the reactor kettle, and 4 mL of sterile water is added, 10 mL of liquid in total. The liquid is uniformly mixed on a heated magnetic stirrer. The temperature is controlled at 80° C., and the reaction is performed for 2 h. The reaction solution is left for standing to cool overnight after the reaction is finished.

Step four, dialysis washing is performed: the complex reaction solution is charged into a dialysis bag (RC membrane, 1 KD, 38 mm), and dialyzed with 1 L of deionized water for 12 h. The deionized water is changed 4 times during dialysis, and unbound zinc ions and other impurities are dialyzed and filtered until the deionized water is clear and transparent.

Step five, freeze drying is performed: the dialyzed reaction solution is charged into a glass screw-top sample bottle, and is dried with a vacuum freeze dryer at −45° C. and 0.02 mBar for 72 h, and the zinc linolenate is obtained with a yield of 75.1%.

The inhibiting effect of zinc linolenate of the present invention on *Helicobacter pylori* is further illustrated in detail by the following embodiments.

1. Material
1.1 Sample
Zinc linolenate is prepared according to Embodiment 2.

1.2 Strain (1) *Helicobacter pylori* strains: standard strains 26695; strains NSH57, MSD132 and G27; levofloxacin, clarithromycin and metronidazole multi-resistant strain (HP159); clinical strain resistant to metronidazole (HP160); clarithromycin-resistant strain (HP161); levofloxacin-resistant strain (HP162); levofloxacin and metronidazole resistant strain (HP163); and clarithromycin and metronidazole resistant strain (HP285) (The strains were provided by Professor Xie Yong of Nanchang University and obtained by the laboratory from the gastric mucosa samples of clinical patients).

(2) Non-*Helicobacter pylori* bacteria: *Staphylococcus aureus* (ATCC6538), *Escherichia coli* (MG1655), *Salmonella typhi* (14028s), *Pseudomonas aeruginosa* (PA01), *Acinetobacter baumannii* (ATCC19606), *Klebsiella pneumoniae* (YF173002), *Enterobacter cloacae* (ATCC13047), *Campylobacter jejuni* (NCTC11168), *Mycobacterium smegmatis* ($MC^2$ 155), *Haemophilus influenzae* (ATCC49766), *Neisseria gonorrhoeae* (ATCC19424), *Bacillus subtilis* (168), *Streptococcus pneumoniae* (ATCC49619), *Proteus mirabilis* (YF163006), *Enterococcus faecalis* (ATCC19434), *Enterococcus faecium* (ATCC19434), *Moraxella catarrhalis* (ATCC25238), *Bacillus cereus, Stenotrophomonas maltophilia, Morganella morganii, Candida albicans, Actinobacillus actinomycetemcomitan, Lactobacillus, Shigella dysenteriae,* and *Listeria* (Part of the unnumbered strains are the strains clinically isolated and identified by the Yifu Hospital of Nanjing Medical University).

1.3 Culture medium and main reagents: Columbia medium, brain heart infusion medium, selective antibiotics (vancomycin, polymyxin B, trimethoprim), serum, omeprazole, amoxicillin, clarithromycin, Gram staining solution, bacterial genomic DNA extraction kit, *Helicobacter pylori* specific CagA gene primer, etc.

1.4 Experimental animal: C57BL/6.

1.5 Main instruments: carbon dioxide incubator, tri-gas incubator, centrifuge, tissue lyser, electronic balance, intragastric administration needle, scissors, etc.

1.6 Consumables: EP tubes, Tips, centrifuge tubes, etc.

2. Method and result 2.1 Detection of minimum inhibitory concentration (MIC, 100 UL system) of zinc linolenate for *Helicobacter pylori* by a broth microdilution method (1) Zinc linolenate (2 mg/mL) is prepared.

(2) MIC plate preparation: 173.6 μL of culture medium is added to a first well, then 6.4 μL of antibacterial drug is added, and doubling dilution is performed to the 7th well; the 8th well is not added with drugs, and 90 μL of culture medium is reserved as a control added with bacteria and without drugs.

(3) Bacterial solution preparation: the *Helicobacter pylori* grown in a log phase on a solid plate is taken to make a bacterial suspension with a BHI culture medium, the absorbance ($OD_{600}$) is adjusted to 0.3 ($1 \times 10^8$ CFU/mL), and the bacterial suspension is diluted 10 times to $1 \times 10^7$ CFU/mL for later use.

(4) Inoculation of bacterial solution: 10 μL of bacterial solution above is taken and added to the 1-8th wells (the concentration of the bacterial solution per well is about $1.0 \times 10^6$ CFU/mL). Culture is performed for 72 h to judge the result. The drug concentrations of the 1-7th wells are 64, 32, 16, 8, 4, 2, and 1 μg/mL, respectively.

(5) Result judgment: the minimum drug concentration that can completely inhibit the growth of bacteria in the wells is taken as the MIC. The experiment only makes sense when the bacteria obviously grow in the 8th well, i.e. the positive control well (without antibiotics). When a single drift occurs in the microdilution method, the maximum drug concentration that inhibits bacterial growth should be recorded. If there are multiple drifts, the results should not be reported and the experiment should be repeated. The experiment is repeated 3 times for each drug.

(6) Results: The results are shown in Table 1.

TABLE 1

The minimum inhibitory concentration (MIC) of zinc linolenate for *Helicobacter pylori*

| Strain | Drug resistance of strains | Zinc linolenate (μg/ml) | | | | | | |
|---|---|---|---|---|---|---|---|---|
| | | 64 | 32 | 16 | 8 | 4 | 2 | 1 |
| HP26695 | Sensitive | − | − | − | − | + | + | + |
| NSH57 | Sensitive | − | − | − | − | + | + | + |
| MSD132 | Sensitive | − | − | − | − | + | + | + |
| G27 | Sensitive | − | − | − | − | − | + | + |
| HP159 | Levofloxacin, clarithromycin and metronidazole resistant | − | − | − | − | + | + | + |
| HP160 | Metronidazole resistant | − | − | − | − | − | + | + |
| HP161 | Clarithromycin resistant | − | − | − | − | + | + | + |
| HP162 | Levofloxacin resistant | − | − | − | − | − | − | + |
| HP163 | Levofloxacin and metronidazole resistant | − | − | − | − | + | + | + |
| HP285 | Clarithromycin and metronidazole resistant | − | − | − | − | + | + | + |

+: Bacterial growth, −: No bacterial growth 2.2 Detection of minimum inhibitory concentration (MIC, 100 UL system) of zinc linolenate for non-*Helicobacter pylori* bacteria by microdilution method (1) Zinc linolenate (2 mg/mL) is prepared.

(2) MIC plate preparation: 167.2 μL of culture medium is added to a first well, then 12.8 μL of antibacterial drug is added, and doubling dilution is performed to the 7th well; the 8th well is not added with drugs, and 90 μL of culture medium is reserved as a control without adding bacteria.

(3) Bacterial solution preparation: the non-*Helicobacter pylori* grown in a log phase on a solid plate is taken to make a bacterial suspension with a BHI culture medium, the absorbance ($OD_{600}$) is adjusted to 0.3 ($1 \times 10^8$ CFU/mL), and the bacterial suspension is diluted 100 times to $1 \times 10^6$ CFU/mL for use.

(4) Inoculation of bacterial solution: 10 μL of bacterial solution above is taken and added to the 1-8th wells (the concentration of the bacterial solution per well is about $1.0 \times 10^5$ CFU/mL). Culture is performed for 72 h to judge the result. The drug concentrations of the first-seventh wells are 128, 64, 32, 16, 8, 4, and 2 μg/mL, respectively.

(5) Result judgment: the minimum drug concentration that can completely inhibit the growth of bacteria in the wells is taken as the MIC. The experiment only makes sense when the bacteria obviously grow in the 8th well, i.e. the positive control well (without antibiotics). When a single drift occurs in the microdilution method, the maximum drug concentration that inhibits bacterial growth should be recorded. If there are multiple drifts, the results should not be reported and the experiment should be repeated. The experiment is repeated 3 times for each drug.

(6) Results: the MIC of zinc linolenate for 25 kinds of non-*Helicobacter pylori* bacteria, including *Staphylococcus aureus*, are all greater than or equal to 128 μg/mL, as shown in Table 2.

TABLE 2

The minimum inhibitory concentration (MIC) of zinc linolenate for non-*Helicobacter pylori* bacteria

| Strain | Drug sensitivity of strains | Dilution of zinc linolenate (μg/ml) | | | | | | |
|---|---|---|---|---|---|---|---|---|
| | | 128 | 64 | 32 | 16 | 8 | 4 | 2 |
| *Staphylococcus aureus* | Sensitive | + | + | + | + | + | + | + |
| *Escherichia coli* | Sensitive | − | + | + | + | + | + | + |
| *Salmonella typhi* | Sensitive | + | + | + | + | + | + | + |
| *Pseudomonas aeruginosa* | Sensitive | + | + | + | + | + | + | + |
| *Acinetobacter baumannii* | Sensitive | + | + | + | + | + | + | + |
| *Klebsiella pneumoniae* | Sensitive | − | + | + | + | + | + | + |
| *Candida albicans* | Sensitive | + | + | + | + | + | + | + |
| *Enterobacter cloacae* | Sensitive | + | + | + | + | + | + | + |
| *Campylobacter jejuni* | Sensitive | + | + | + | + | + | + | + |
| *Mycobacterium smegmatis* | Sensitive | + | + | + | + | + | + | + |
| *Actinobacillus actinomycetemcomitans* | Sensitive | + | + | + | + | + | + | + |
| *Haemophilus influenzae* | Sensitive | + | + | + | + | + | + | + |
| *Neisseria gonorrhoeae* | Sensitive | + | + | + | + | + | + | + |
| *Bacillus subtilis* | Sensitive | + | + | + | + | + | + | + |
| *Streptococcus pneumoniae* | Sensitive | + | + | + | + | + | + | + |
| *Proteus mirabilis* | Sensitive | + | + | + | + | + | + | + |
| *Enterococcus faecalis* | Sensitive | − | + | + | + | + | + | + |
| *Enterococcus faecium* | Sensitive | + | + | + | + | + | + | + |
| *Lactobacillus* | Sensitive | − | + | + | + | + | + | + |
| *Moraxella catarrhalis* | Sensitive | + | + | + | + | + | + | + |
| *Bacillus cereus* | Sensitive | + | + | + | + | + | + | + |
| *Stenotrophomonas maltophilia* | Sensitive | − | + | + | + | + | + | + |
| *Morganella morganii* | Sensitive | − | + | + | + | + | + | + |
| *Shigella dysenteriae* | Sensitive | − | + | + | + | + | + | + |
| *Listeria* | Sensitive | + | + | + | + | + | + | + |

+: Bacterial growth, −: No bacterial growth 2.3 Construction of animal models to detect the inhibiting effect of zinc linolenate on *Helicobacter pylori* in vivo 2.3.1 Drugs: Zinc linolenate, omeprazole, amoxicillin, and clarithromycin, all dissolved to 10 mg/mL.

2.3.2 Strain: A clinically isolated strain (BHK159), multi-resistant to levofloxacin, clarithromycin and metronidazole, domesticated 3 times in the laboratory, and confirmed that is can colonize in the gastric mucosa of mice.

2.3.3 Animal modeling:

(1) Animal grouping: 10 of 50 mice are randomly selected into a negative control group, and the other 40 mice are in an infection group. Each group of mice is weighed and the average weight is calculated.

(2) Mice intragastric administration: 40 mice in the infection group fast for 12 hours before intragastric administration, and then are intragastrically administered with the *Helicobacter pylori* suspension prepared by BHI. The absorbance ($OD_{600}$) of the bacterial solution is 3 ($1 \times 10^9$ CFU/mL). Each mouse is administered with 0.5 mL of *Helicobacter pylori* suspension, and fasts for 4 hours after intragastric administration. Intragastric administration is performed once every other day for 5 consecutive times.

(3) Model inspection: 14 days after the intragastric administration for the last time, the mice in the infection group and the control group are weighed to calculate the average weight. 3 mice in the infection group are randomly selected, and fast for 12 hours, blood is taken from the eyeballs, and the mice are sacrificed by cervical dislocation. The mice are dissected for the stomach, and part of the stomach tissue is stored in formalin for pathological examination; and the other part of the stomach tissue is weighed, homogenized and diluted 10, 100, 1000 times, then spread evenly on Columbia medium plates containing 10% serum with inoculating loops, and placed in a tri-gas incubator (10% $CO_2$, 5% $O_2$ and 85% $N_2$) for 72-96 h. The characteristics of bacterial colonies on the culture medium are observed, and the number of transparent colonies of needle-tip-like size is counted.

(4) Strain identification: A needle-tip-sized transparent colony is taken from the culture for Gram staining microscopy; bacterial DNA is extracted, a *Helicobacter pylori* specific gene CagA primer is used to perform PCR amplification, and the amplified product is detected by 1.0% agarose gel electrophoresis; and the stomach tissue is sectioned in paraffin and subjected to HE staining inspection.

(5) Inspection and identification results: The colonization amount in the stomach tissue of each mouse is in a range of $1 \times 10^5$ to $1 \times 10^6$ CFU/g, see Table 3 for details.

Pathological damage of the gastric mucosa is detected by HE staining inspection, accumulation of gastric mucosal inflammatory cells is found, and local mucosa has erosion; the culture has a typical *Helicobacter pylori* morphology as detected by Gram staining inspection; and the culture is identified as *Helicobacter pylori* by PCR amplification. The results are summarized in Table 3, and can prove that the modeling is successful.

2.3.4 Observation of therapeutic effects of drugs:

(1) Animal grouping: the experimental group divides the successfully molded infection group into 4 groups, namely an omeprazole plus zinc linolenate group, an omeprazole plus amoxicillin and clarithromycin group (triple treatment group), a zinc linolenate group, and a PBS group, each containing 6 mice; and a negative control group contains 6 mice without *Helicobacter pylori* infection.

TABLE 3

Validation of modeled mice

| Mice | Colonization amount (CFU/g) | HE staining inspection | Gram stain inspection | PCR identification |
|---|---|---|---|---|
| Infected mice 1 | $3 \times 10^6$ | Inflamed | + | + |
| Infected mice 2 | $6 \times 10^5$ | Inflamed | + | + |
| Infected mice 3 | $3.5 \times 10^5$ | Inflamed | + | + |
| Uninfected mice 1 | 0 | Un-inflamed | − | − |
| Uninfected mice 2 | 0 | Un-inflamed | − | − |
| Uninfected mice 3 | 0 | Un-inflamed | − | − |

+: Identified as *Helicobacter pylori*,
−: Unidentified as *Helicobacter pylori*

(2) Animal administration: the experimental group is intragastrically administered. The group with omeprazole is administered with omeprazole first, and then administered with other drugs 30 min later. After the mice are administered with the drugs, the mice fast for 4 hours. Calculated according to an average of 20 g/mouse of the weight of mice, the dosage is: omeprazole 138.2 mg/kg, amoxicillin 28.5 mg/kg, clarithromycin 14.3 mg/kg, and zinc linolenate 24 mg/kg, once a day for 5 consecutive times. The negative control group is administered with a PBS solution with the same dosage and number of times as above.

(3) Efficacy test: the mice in the infection group are weighed and the average weight is calculated on the 2 days after the drug is stopped. Blood is taken from the eyeballs and the mice are sacrificed by cervical dislocation. Stomach tissue is taken, and the isolation, culture and identification of *Helicobacter pylori* are the same as in 2.3.3 (3) and (4).

Figure 1:
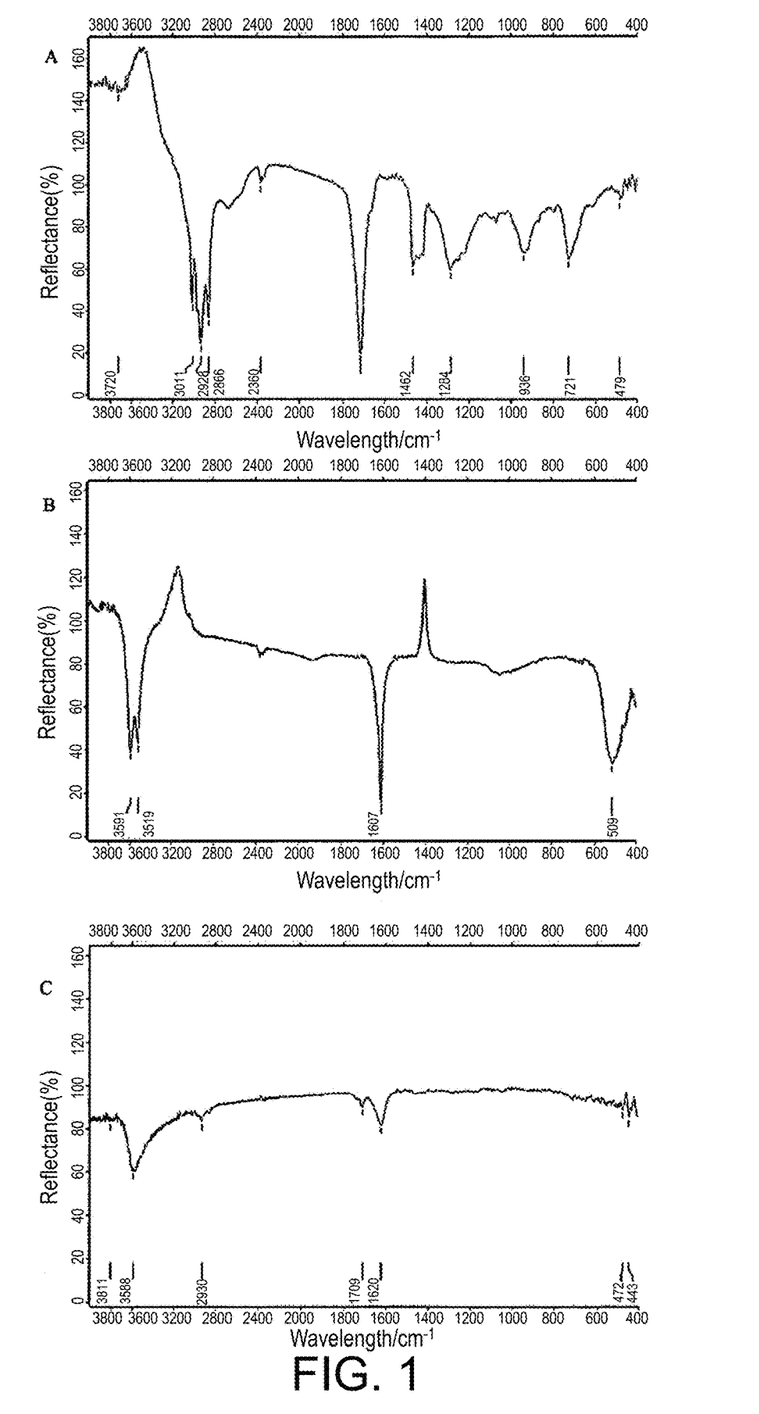
FIG. 1 shows the Fourier infrared spectrum of zinc linolenate. A is linolenic acid, B is zinc chloride, and C is zinc linolenate.
Figure 2:
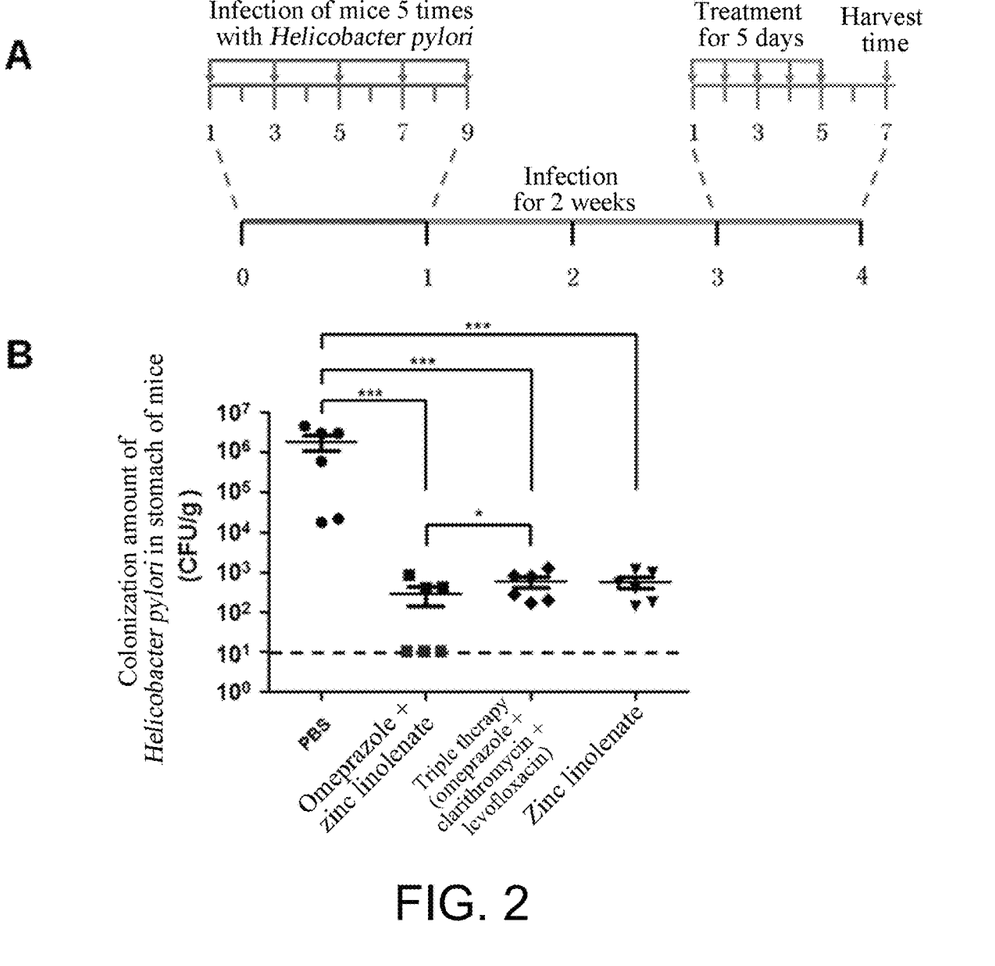
FIG. 2 shows the inhibiting effect of zinc linolenate on *Helicobacter pylori* in mice. A. Schematic image of establishment of acute gastritis animal models with mice infected with *Helicobacter pylori* and drug treatment; B. Colonization of *Helicobacter pylori* in the gastric mucosa of mice after treatment in each treatment group.
Figure 3:
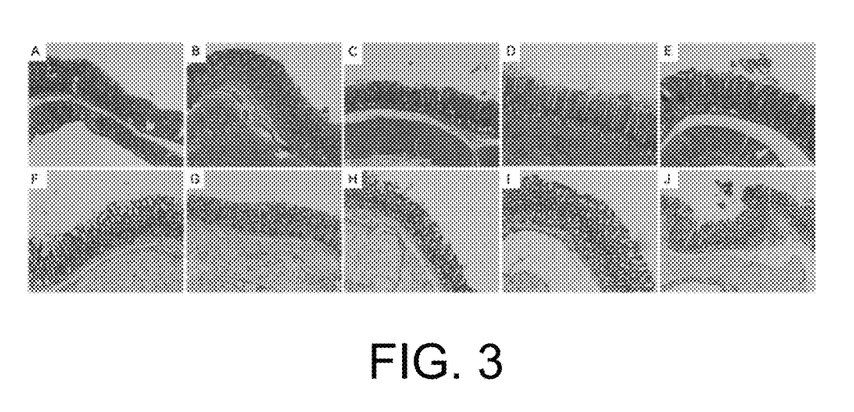

(4) Therapeutic effect: the inhibition of *Helicobacter pylori* in the omeprazole plus zinc linolenate group is significantly better than that of the triple therapy group (omeprazole plus amoxicillin and clarithromycin) (P<0.05), as shown in FIG. 2. The ability of the omeprazole plus zinc linolenate group to repair inflammatory gastric mucosal damage is significantly better than that of the triple therapy group, as shown in FIG. 3.

2.4 Toxicity detection of zinc linolenate 2.4.1 Cytotoxicity detection (1) Ges-1 and AGS cell suspensions are prepared, and the concentration is adjusted to $1\times10^6$.

(2) Inoculation into a 96-well plate: 100 μL is added per well, and 3 replicates is performed for the same sample.

(3) Culture is performed for 12 hours in an incubator at 37° C.

(4) 10 μL of zinc linolenate, 10 μL of linolenic acid, and 10 μL of zinc chloride are added respectively, and the working concentrations are 400 μg/mL, 300 μg/mL, 200 μg/mL, 100 μg/mL, and 0 μg/mL, respectively. A group added with drugs and without cells and a PBS control group are set.

(5) Culture is performed for 12 hours in an incubator at 37° C.

(6) 10 μL of CCK-8 is added, mixed by tapping and incubated for 4 hours.

(7) The absorbance at 450 nm is measured, and the survival rate is calculated according to the formula: cell proliferation rate[(As−Ab)]/[(Ac−Ab)]×100%, wherein As are wells containing the cell culture medium, drugs, and CCK-8; Ac are wells containing the cell culture medium, CCK-8, and no drug; and Ab are wells containing no cells and drugs, but only the culture medium and CCK-8. A survival curve is established based on the survival rate.

Figure 4:
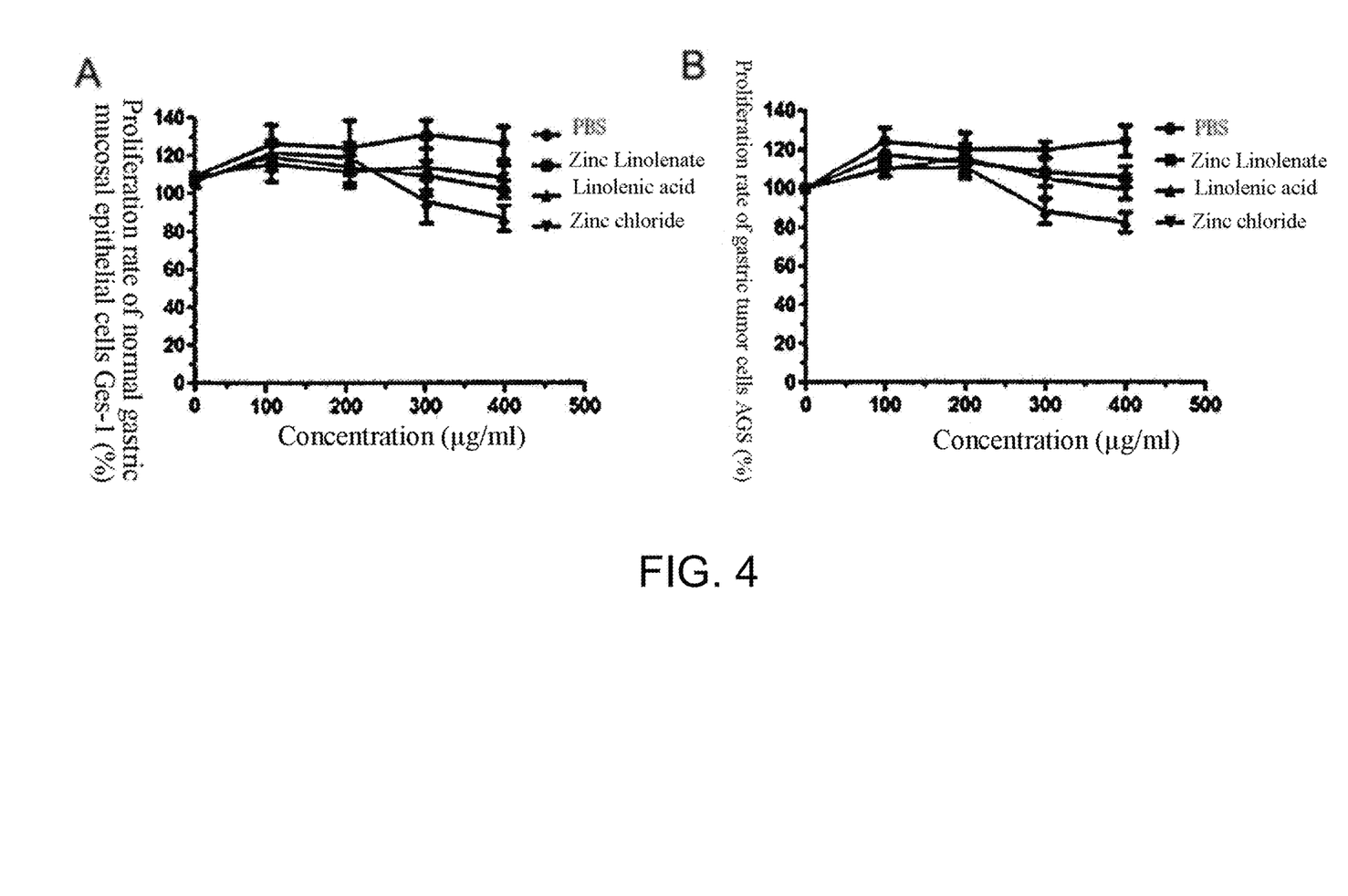
FIG. 4 shows detection of the cytotoxicity of zinc linolenate on Ges-1 and AGS in vitro.

(8) Results: the 400 μg/mL zinc linolenate has little damage to Ges-1 and AGS cells, and the toxicity is smaller than that of linolenic acid. See FIG. 4.

2.4.2 Animal toxicity (1) Preparation of mice: 20 8-week-old C57BL/6 mice are randomly divided into an administration group containing 10 mice and a negative control group containing 10 mice.

(2) Intragastric administration: administration is performed with 10 times the therapeutic dose of zinc linolenate, that is, administration is performed according to 240 mg/kg per mouse, once a day for 3 consecutive days. The negative control group is administered with a PBS solution, and the number of times and dose are same as those in the administration group.

(3) Weighing of weight: the weight of mice is weighed 1 day before administration for 7 consecutive days.

(4) Efficacy test: the mice in the infection group are weighed 3 days after the drug is stopped, and the average weight is calculated. Blood is taken from the eyeballs, and the mice are sacrificed by cervical dislocation. Stomach, kidney, liver and spleen tissues are taken, pathologically sectioned and HE stained, and serum is tested for liver and kidney functions.

Figure 5:
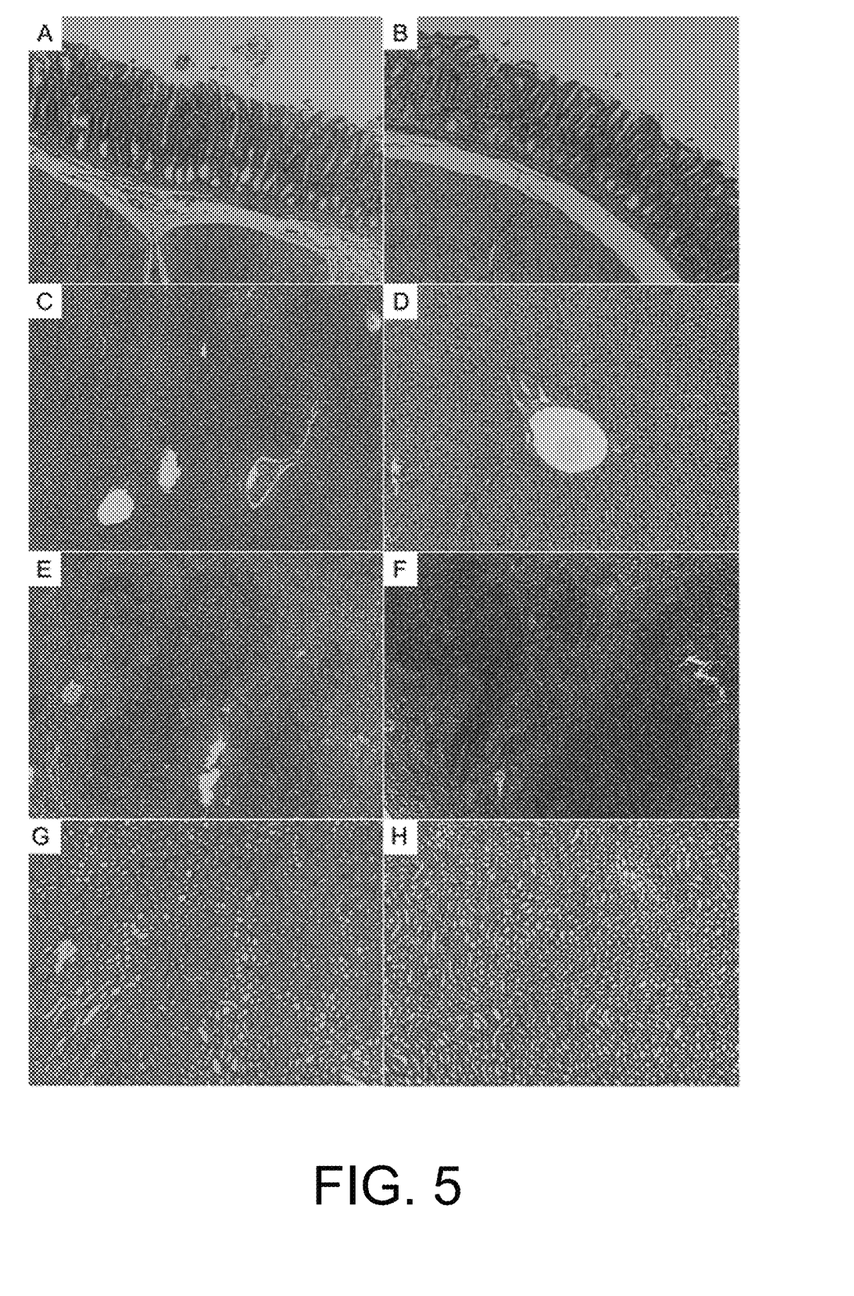
FIG. 5 shows the damage to the mucosal cells of the stomach, liver, kidney and spleen of mice by 10 times the therapeutic dose of zinc linolenate in vivo, wherein A, C, E, and G are HE staining of the tissues of the stomach, liver, spleen and kidney of normal mice, ×100; and B, D, F, and H are HE staining of the tissues of the stomach, liver, spleen and kidney of mice administrated with 10 times the therapeutic dose of zinc linolenate, ×100.
Figure 6:
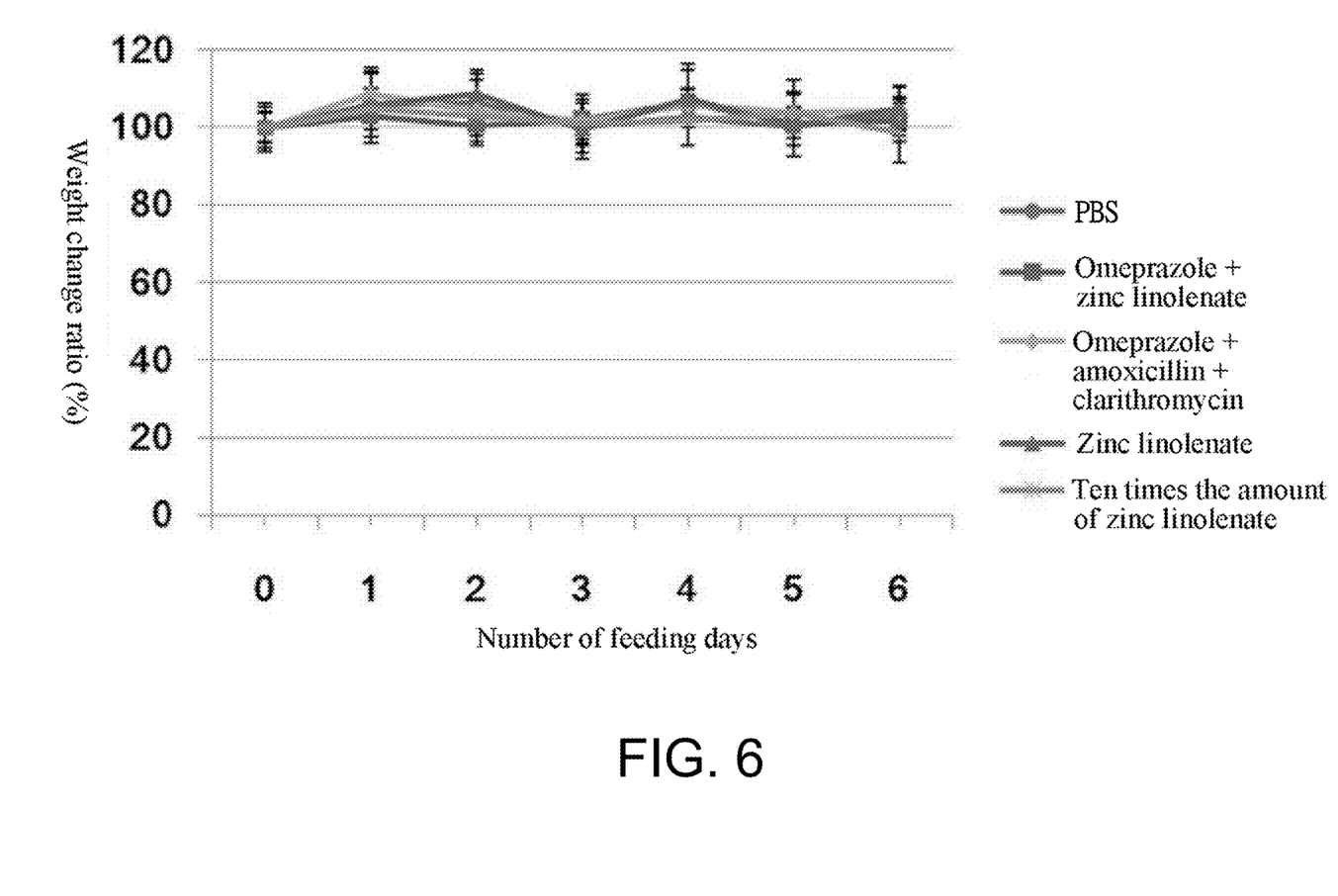
FIG. 6 shows the effect of 10 times the therapeutic dose of zinc linolenate on the weight of mice.

(5) Results: there is no damage to the stomach, kidney, liver and spleen tissues of the mice in the administration group with 10 times the therapeutic dose of zinc linolenate and the negative control group, as shown in FIG. 5. The weight of the mice in the experimental group does not change significantly, as shown in FIG. 6. The liver and kidney functions of the mice in the experimental group are normal, as shown in Table 4.

TABLE 4

Effects of 10 times the therapeutic dose of zinc linolenate on blood biochemical indexes of liver and kidney functions in mice

| Experiment group | Alanine amino-transferase (U/L) | Aspartate amino-transferase (U/L) | Blood urea nitrogen (mmol/L) | Creatinine (μmol/L) |
|---|---|---|---|---|
| Omeprazole + Zinc linolenate | 19.67 ± 1.53 | 117.00 ± 22.61 | 10.27 ± 0.32 | 16.33 ± 0.58 |
| Omeprazole + Amoxicillin + Clarithromycin | 34.33 ± 113.43 | 22.00 ± 58.40 | 8.77 ± 1.23 | 17.00 ± 1.00 |
| zinc linolenate | 50.00 ± 23.00 | 192.33 ± 74.74 | 14.97 ± 3.28 | 18.33 ± 3.06 |
| PBS | 22.00 ± 4.36 | 110.00 ± 14.73 | 13.90 ± 3.72 | 16.67 ± 1.15 |
| Not infected (10 times the dose of zinc linolenate) | 23.33 ± 0.58 | 138.33 ± 23.18 | 11.90 ± 0.79 | 15.00 ± 2.00 |
| Not infected (not administered) | 29.00 ± 6.93 | 231.00 ± 97.25 | 13.13 ± 1.42 | 18.33 ± 5.69 |

What is claimed is:

1. A preparation method of zinc linolenate, comprising the following steps:
    step one, activation of zinc chloride: dissolving zinc chloride in sterile water, and reacting the zinc chloride solution in a reactor kettle at 150-170° C. for 30-60 min, and then naturally cooling the zinc chloride solution to room temperature;
    step two, activation of linolenic acid: dissolving 1-ethyl-3-(3-dimethylaminopropyl)carbodiimide hydrochloride (EDC), N-hydroxysulfosuccinimide sodium salt (NHS) and linolenic acid in a molar ratio of (2-4):(2-4):1 in an EMS solvent and performing activation in nitrogen gas for 30 min;
    step three, complex reaction: reacting the activated zinc chloride in the step one and the activated linolenic acid in the step two in a molar ratio of 1:(1.8-2) at 70-80° C. for 2-3 h, then leaving the reaction solution for standing for 6-12 h after the reaction is finished;
    step four, dialysis filtration: performing dialysis using a dialysis bag in pure water for 12-14 h until the pure water is clear and transparent; and
    step five, freeze drying: performing drying using a vacuum freeze dryer for 48-72 h to obtain zinc linolenate.

2. The preparation method of zinc linolenate of claim 1, wherein a concentration of the aqueous solution of zinc chloride is 1 mol/L.

3. The preparation method of zinc linolenate of claim 1, wherein the molar ratio of the 1-ethyl-3-(3-dimethylaminopropyl)carbodiimide hydrochloride (EDC) to the N-hydroxysulfosuccinimide sodium salt (NHS) to the linolenic acid is 4:4:1.

4. The preparation method of zinc linolenate of claim 1, wherein the molar ratio of the activated zinc chloride to the activated linolenic acid is 1:1.8.

* * * * *